(12) United States Patent
Scamilla Aledo et al.

(10) Patent No.: US 6,599,525 B2
(45) Date of Patent: Jul. 29, 2003

(54) DRESSINGS AND BANDAGES COMPRISING SAME

(75) Inventors: Maria Aparecida de Carvalho Scamilla Aledo, Sao Jose dos Campos (BR); James J. Meizanis, Somerville, NJ (US); d'Artagnan Silva de Oliveira, Sao Jose dos Campos (BR); Fabio Eduardo Franca Rangel, Jacarei (BR)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 10/200,843

(22) Filed: Jul. 22, 2002

(65) Prior Publication Data
US 2003/0086963 A1 May 8, 2003

Related U.S. Application Data

(63) Continuation of application No. 09/752,023, filed on Dec. 28, 2000, which is a continuation of application No. 09/608,412, filed on Jun. 30, 2000, now abandoned, which is a continuation of application No. 09/199,142, filed on Nov. 24, 1998, now abandoned.

(51) Int. Cl.[7] .............. A61L 15/00; A61F 13/00
(52) U.S. Cl. .............. 424/445; 424/443; 424/446; 424/447; 424/448; 424/449
(58) Field of Search .............. 424/445, 443, 424/446, 447, 448, 449

(56) References Cited

U.S. PATENT DOCUMENTS

| 5,147,339 A | 9/1992 | Sundstrom |
| 5,814,031 A | 9/1998 | Mooney et al. |
| 6,072,100 A | * 6/2000 | Mooney et al. .............. 602/48 |
| 2001/0031370 A1 | * 10/2001 | Kundel .............. 428/515 |

* cited by examiner

*Primary Examiner*—Thurman K. Page
*Assistant Examiner*—I. Ghali

(57) ABSTRACT

The dressings of the invention comprise at least two components: an absorbent substrate having a first skin-facing surface and a second opposing surface; and a discontinuous coating of a semi-solid composition having an ointment-like feel overlying a portion of the first surface of said absorbent substrate. The absorbent substrate is useful as a passive dispenser of at least one active ingredient that may be contained therein. The discontinuous coating is essentially non-adherent to the skin and is useful as an active dispenser of at least one active ingredient that may be contained therein. In preferred embodiments the dressing of the invention contains at least one and more preferably at least two active ingredients intended to provide therapeutic benefit to the skin.

7 Claims, 9 Drawing Sheets

DRESSINGS AND BANDAGES COMPRISING SAME

CROSS REFERENCE TO RELATED APPLICATIONS

This is a continuation of application Ser. No. 09/752,023, filed Dec. 28, 2000, which is a continuation of Application Ser. No. 09/608,412, filed Jun. 30, 2000, now abandoned, which is a continuation of application Ser. No. 09/199,142, filed Nov. 24, 1998, now abandoned.

FIELD OF THE INVENTION

The present invention is directed to a dressing, particularly for wounds, which comprises an absorbent substrate and a discontinuous coating of a composition having an ointment-like feel. The dressing is useful for absorbing bodily exudates, particularly wound exudates, and for dispensing active ingredients, for example, therapeutics, to the skin with no substantial loss of absorption capacity. The dressings of the invention and bandages derived therefrom may be easily and comfortably removed from the skin when desired without re-traumatizing a wound site.

BACKGROUND OF THE INVENTION AND PRIOR ART

Bandages and wound dressings typically comprise an absorbent pad to absorb exudate from a wound. The absorbent pad is typically constructed of a fibrous nonwoven material. One problem with such absorbent bandages is that the fibers of the absorbent pad may become embedded in the healing wound, making it difficult to painlessly remove the bandage without traumatizing the wound. To overcome this problem, absorbent pads used in bandages are typically covered with a porous plastic film to prevent the pad from sticking to the wound.

It is common practice to treat wounds with ointment-like compositions. Ointments are often used because they tend to act as salves that soothe the wound.

Furthermore, ointments may be compounded with active ingredients such as antibiotics to provide therapeutic properties to assist in infection control and wound healing. Because ointments are usually viscous liquids or semi-solids rather than solid materials, therapeutic materials present in an ointment are usually readily available to the wound merely by contact of the wound with the ointment, even in the absence of wetness such as moist wound exudate.

After treatment with an ointment, wounds are typically covered with an adhesive bandage. The use of an ointment in conjunction with a bandage is also beneficial because the ointment tends to prevent the fibers of an absorbent pad present in a bandage from becoming attached to the wound site. While effective at promoting wound healing, a problem with such treatment regimens is that they are relatively inconvenient and messy.

An advancement in the art of wound treatment was the development of structured occlusive dressings of the type described in U.S. Pat. No. 5,814,031, which is incorporated herein in its entirety by reference. The dressings of the '031 patent comprise a support material and an occlusive composition overlying the support material. Exemplary support materials described in the '031 patent include woven, knitted and nonwoven fabrics. While these support materials may have some absorptive capacity, the presence of the occlusive composition overlying the support material tends to block the support and prevent it from absorbing moisture-containing fluids such as wound exudate.

Japanese Laid Open Patent Application 56-2909 discloses an adhesive drug material that is administered in the form of a poultice or drug patch. The adhesive drug material is applied to an air-permeable base material in the form of spots, nets or lines, by, e.g., a printing method. The application of the adhesive drug material to the base material in a discontinuous pattern is said to prevent maceration damage to the skin. However, the use of an adhesive material in the wound area of a wound dressing would be expected to be undesirable because contact of the wound with an adhesive composition would be expected to re-traumatize the wound when the dressing is removed.

UK Patent GB 2,221,620 discloses a hemostatic wound dressing material of a fibrous substrate having a discontinuous coating of an aqueous solution of an alginate material deposited on the surface thereof. The final step in the manufacture of the dressing is evaporating the water from the alginate solution, as, for example, by passage of the dressing material through temperature controlled ovens. While the dressings disclosed in the '620 patent may possess good hemostatic properties, they are not expected to have the soothing properties of ointment-containing dressings. Furthermore, any actives present in such dressing would not be expected to be readily available to a wound without moisture such as that which is contained in wound exudate.

U.S. Pat. Nos. 4,166,108 and 4,331,653 disclose compositions in the form of a lotion or cream to curtail bleeding of the skin. It is stated that these compositions may be impregnated into pre-packaged bandages. Impregnation of these compositions into bandages would again be expected to block the absorptive capacity of the bandages, and would thus prevent the bandages from absorbing wound exudate.

U.S. Pat. No. 5,147,339 discloses wound treatment dressings comprising corpuscles containing bioactive substances in a hydrophilic medium dispersed in a solid, hydrophobic, water insoluble continuous matrix. Because the active substance is distributed in a solid matrix, it is expected that wound exudate or other moisture-containing substances would be required to release the bioactive substance from the matrix and into contact with the wound. Furthermore, the '339 dressing would not be expected to have the wound soothing properties of ointment-containing dressings.

It is an object of the present invention to provide a dressing for treating wounds that can be removed easily from a wound site when desired without retraumatizing the wound.

It is another object of the invention to provide a dressing that has a soothing effect on wounds.

It is another object of the invention to provide a dressing that is capable of delivering active therapeutic ingredients to a wound site.

It is another object of the invention to provide a dressing that is capable of delivering multiple therapeutic ingredients to a wound site, even when such ingredients are not mutually compatible.

It is another object of the invention to provide a dressing that is capable of absorbing wound exudate.

It is another object of the invention to provide a dressing containing a soothing ointment-like composition while being capable of absorbing wound exudate.

It is another object of the invention to provide a dressing that exhibits all or a combination of the aforesaid attributes.

It is another object of the invention to provide a dressing with the aforesaid attributes in the form of an adhesive bandage.

Additional objects will become evident in the ensuing description of the invention.

SUMMARY OF THE INVENTION

The dressings of the invention comprises at least two components:

a. an absorbent substrate having a first skin-facing surface and a second opposing surface; and b. a discontinuous coating of a semi-solid composition having an ointment-like feel overlying a portion of the first surface of said absorbent substrate.

The absorbent substrate in the dressing of the invention is useful as a passive dispenser of at least one active ingredient. The discontinuous coating is essentially non-adherent to the skin and is useful as an active dispenser of at least one active ingredient.

In a preferred embodiment, the dressing of the invention contains at least one active ingredient intended to provide therapeutic benefit to the skin. In another preferred embodiment, the dressing of the invention contains at least two active ingredients, the first being substantially contained within the absorbent substrate, and a second active ingredient contained substantially within the discontinuous coating.

Also included within the scope of the invention are adhesive bandages comprising a backing material, an adhesive layer and the above-enumerated dressings.

BRIEF DESCRIPTION OF THE DRAWINGS

FIG. 1B is a cross-sectional view of the dressing of FIG. 1a taken along line 2—2 of FIG. 1a.

FIG. 2C shows yet another alternate configuration of the

DETAILED DESCRIPTION OF THE INVENTION

The absorbent substrate in the dressing of the invention is useful as a passive dispenser to deliver at least one ingredient to the skin, as for example, to a wound site. As used herein, the term "passive dispenser" means that an active, e.g., therapeutic ingredient, when present in the absorbent substrate, is only sparingly if at all dispensed from the substrate in the absence of moisture. When moisture, as contained in wound exudate for example, contacts the absorbent substrate, it causes dissolution of any active ingredient present in the absorbent substrate, thereby enabling the active to migrate to the skin or wound surface.

The discontinuous coating in the dressing of the invention is useful as an active dispenser of at least one active ingredient from the dressing of the invention. As used herein, the term "active dispenser" means that an active ingredient, when present in the discontinuous coating, is readily available to the skin by mere contact, even in the absence of wetness, blood or wound exudate. In the absence of moisture, actives present in the discontinuous coating are believed to be more readily available to the skin than those present in the absorbent substrate due to the faster rates of diffusion of an active in the semi-solid, semi-liquid composition comprising the discontinuous coating relative to the slower diffusion rates present in a solid absorbent substrate layer.

While the compositions used in the discontinuous coating in the dressing of the invention may possess some degree of tackiness, the discontinuous coating is substantially non-adherent to the skin. This means that the dressings of the invention would not sufficiently adhere to skin to remain in place during use without additional components such as a gauze wrap or an adhesive-coated backing. The non-adherent nature of the coating composition assures that the dressings of the invention would be readily removable from a wound when removal is desired without adversely affecting the healing wound.

Figure 1A:
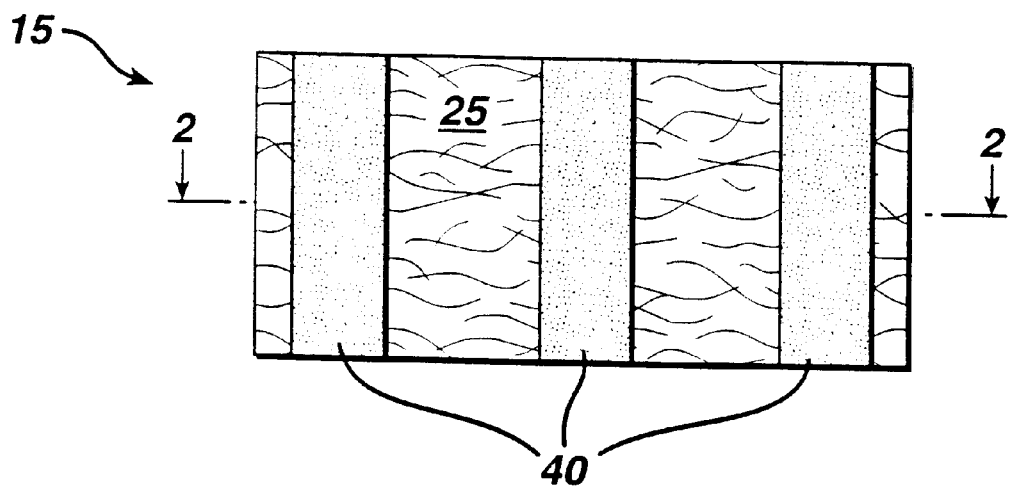
FIG. 1A is a top plan view of one embodiment of the dressing of the invention.
Figure 1B:
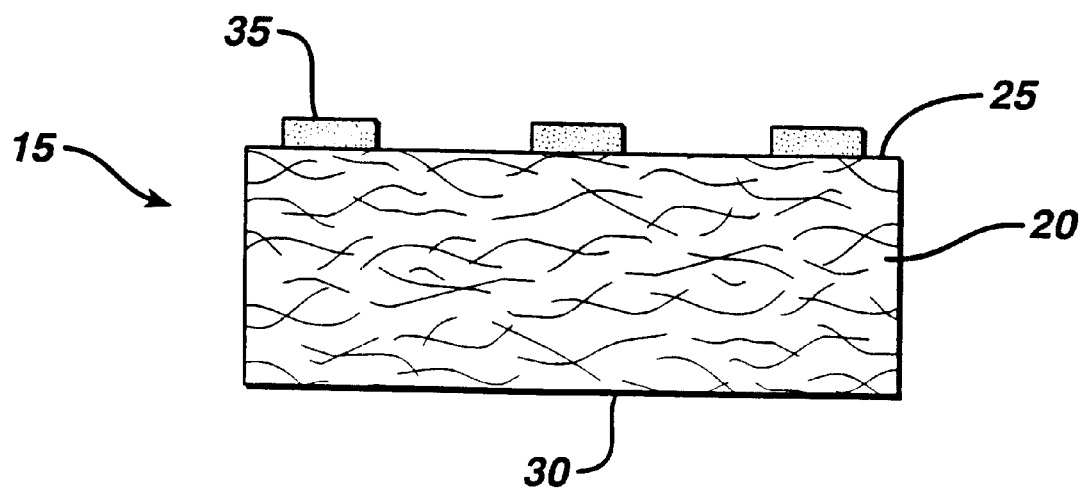

FIG. 1A and FIG. 1B show one embodiment of the dressing of the invention in top plan view and in cross-section along line 2—2 of FIG. 1A, respectively. Dressing 15 is comprised of absorbent substrate 20 having skin-facing surface 25 and opposing surface 30. Dressing 15 is further comprised of a discontinuous coating 35 overlying a portion of the surface of absorbent substrate 20. In the embodiment shown in FIG. 1, the coating is shown in the form of equal-width stripes 40 arranged in a regular, equally spaced pattern across skin-facing surface 25 of absorbent substrate 20. While FIG. 1B shows coating 35 overlying the surface of absorbent substrate 20 without penetrating below said surface, it will be understood that coating 35 may partially penetrate into absorbent substrate 20 so long as some amount of the coating 35 overlies at least some portion of skin-facing surface 25 of substrate 20.

Figure 2A:
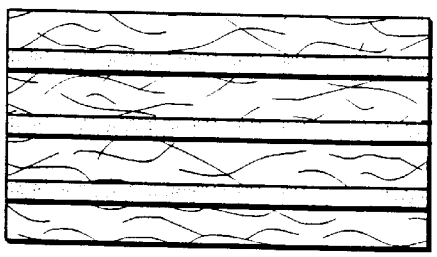
FIG. 2A shows one configuration of the discontinuous coating of the dressing of the invention.
Figure 2B:
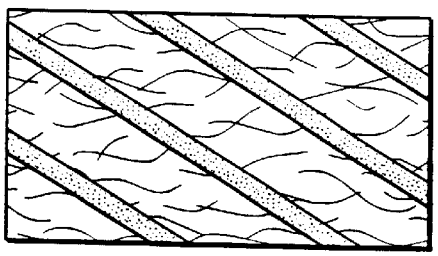
FIG. 2B shows an alternate configuration of the discontinuous coating of the dressing of the invention.
Figure 2C:
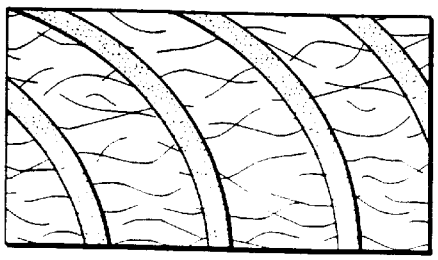
Figure 2D:
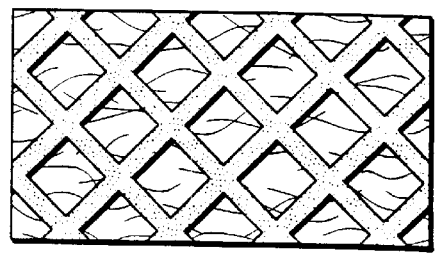
FIG. 2D shows yet another alternate configuration of the discontinuous coating of the dressing of the invention.
Figure 2E:
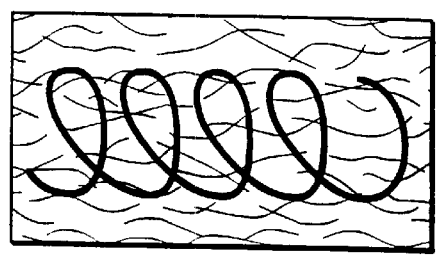
FIG. 2E shows yet another alternate configuration of the discontinuous coating of the dressing of the invention.
Figure 2F:
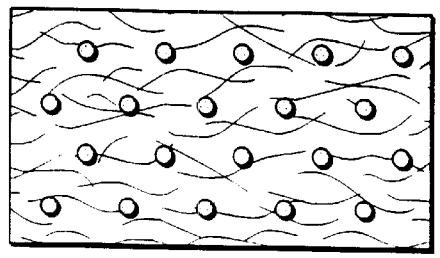
FIG. 2F shows yet another alternate configuration of the discontinuous coating of the dressing of the invention.

Coating 35 may be applied to substrate 20 in either a regular pattern or a random pattern. For example, coating 35 may be configured in either a regular or random pattern of elements such as straight lines, angled lines, curved lines, intersecting lines, dots, circles and geometric shapes, or in a combination of these elements. FIG. 2A through FIG. 2F show alternate embodiments of the dressing of the invention wherein the coating is configured as a series of lines or stripes parallel to the longitudinal axis of the dressing (FIG. 2A), as a series of lines or stripes at an angle to the axis of the dressing (FIG. 2B), as a series of curved stripes (FIG. 2C), as a series of intersecting lines in a cross-hatch pattern (FIG. 2D), as a swirling line (FIG. 2E) and as a series of dots (FIG. 2F).

The coating may be applied to the substrate using techniques well known in the art such as printing, spraying, reverse roll or knife-over-roll coating or extrusion coating techniques.

The absorbent substrates used in the dressings of the invention may be selected from woven fabrics, knitted fabrics nonwoven fabrics and foams. A nonwoven fabric is the preferred substrate for use in the dressings of the invention.

By applying the coating composition to the substrate in a discontinuous pattern, a portion of the skin-facing surface of the absorbent substrate remains exposed to the skin to permit absorption of fluid such as wound exudate by the absorbent substrate. In order to provide the soothing effects of the coating composition but still provide access to the surface of the absorbent substrate, the coating composition should be applied so as to overly from about 1% to about 99% of the skin-facing surface area of the absorbent substrate. Preferably, the coating should overly from about 10% to about 90% of the skin-facing surface area of the absorbent substrate. Most preferably, the coating should overly from about 20% to about 80% of the skin-facing surface area of the absorbent substrate.

Figure 3:
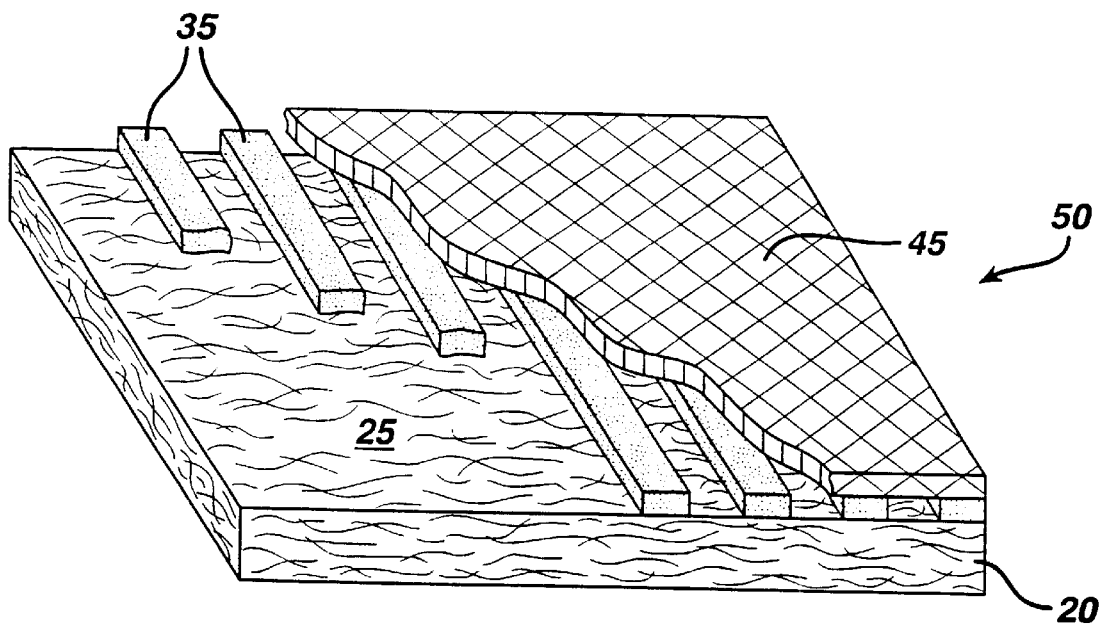
FIG. 3 is a perspective drawing with parts cut away of another embodiment of the dressing of the invention wherein the dressing further comprises a porous covering material overlying the discontinuous coating.
Figure 4:
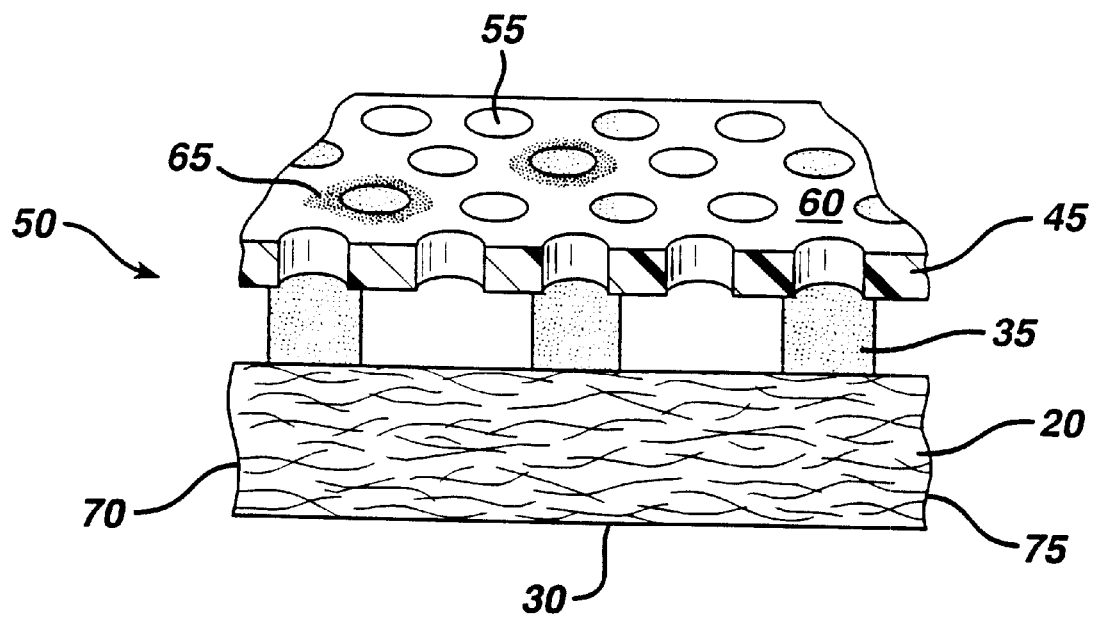
FIG. 4 is a fragmentary view, greatly enlarged and partially in section of a portion of the dressing of FIG. 3.

The dressings of the invention may also comprise a porous covering material overlying the discontinuous coating. A dressing of the invention comprising a porous covering material is illustrated in FIGS. 3 and 4. Dressing 50 comprises an absorbent substrate 20 and a discontinuous coating 35 overlying a portion of surface 25 of substrate 20. The dressing further comprises porous covering material 45 overlying coating 35. Porous covering material 45 may comprise a porous polyethylene film, net or mesh, an example of which is available from Hercules, Inc., of Wilmington, Del., U.S.A. under the designation DELNET X-550. Other porous covering materials may be used in place of the aforementioned porous polyethylene films available under the DELNET name. For example, the porous covering material can be made of polyvinyl chloride, polypropylene, polyester, nylon or the like polymeric materials instead of polyethylene.

It will be understood that in some instances, depending on such factors as the manufacturing conditions employed and the Theological characteristics of the composition comprising discontinuous coating 35, some of the coating composition may pass upwardly into holes 55 of porous covering material 45 and may spread to some extent over the upper surface 60 of porous covering material 45. Portions of the composition which have spread over the upper surface of the porous covering material are identified by numeral 65 in FIG. 4.

The porous covering material 45 is shown in FIG. 3 and in FIG. 4 as being substantially coextensive with the absorbent substrate 20. It will be understood that porous covering material may extend beyond the upper surface of the dressing and along sides 70, 75 of the absorbent substrate. Porous covering material 45 may further extend around substrate 20 such that it is in contact with second surface 30 of absorbent substrate 20.

Porous covering material 45 is shown in FIG. 3 and in FIG. 4 as spanning across the composition comprising the discontinuous coating 35 and not in direct contact with upper surface 25 of substrate 20. It will be understood that porous covering material 45 may, in fact, directly contact portions of the upper surface 25 of substrate 20. The degree to which the porous covering material 45 directly contacts substrate surface 25 will depend on such factors as the thickness of the coating, the extent to which the coating covers the substrate surf ace, the pattern of the coating and the stiffness of the porous covering material.

The compositions comprising the coatings used in the dressings of the invention preferably contain a hydrophobic solvent or a combination of hydrophobic solvents and other additives resulting in a structured dressing that does not readily flow. The structured dressings of this invention may comprise an oil-phase composition or a water-in-oil emulsion. The compositions may be hydrophobic or hydrophilic, although hydrophobic and/or oleophilic compositions are preferred in the dressings of the invention.

The hydrophobic solvent may be a hydrocarbon material, such as petrolatum, mineral oil or the like. It may also be composed of fatty acid-derived materials such as castor oil or the like. Alternatively, the hydrophobic solvent constituent may contain a wax in addition to other solvents, such as paraffin wax, microcrystalline wax, beeswax or the like. The hydrophobic solvent serves as the "oil base" of the composition or the emulsion and makes up a large proportion of the composition, up to about 90% by weight. This solvent imparts the ointment-like "feel" to the composition, contributes to the regulation of delivery of active materials such as therapeutics that may be present in the composition, and is the primary means by which the dressings of this invention achieve superior wound release characteristics. Preferably, the solvent is a fluid, semi-solid or solid at room or skin temperature (from about 55° F. to about 100° F.) having a viscosity of from about 1 to about 100,000 centipoise. Thus, any hydrocarbon material or combination of materials which have the appropriate viscosity at the desired temperatures may be used in the products of this invention.

As will be evident to those skilled in the art, in order to prevent the compositions used in the dressing of the invention from migrating beyond the outer perimeter of the dressing during storage and use, the compositions preferably have a viscosity of at least about 10,000 centipoise at physiological temperatures. More preferably, the compositions have a viscosity of at least about 20,000 centipoise, and most preferably, the compositions have a viscosity of at least about 30,000 centipoise at physiological temperatures.

A combination of members of two classes of polymers and/or additives is preferably added to the hydrophobic solvent to make the compositions used in the dressings of this invention. The first class of polymers can be generally termed "network" polymers. These polymers increase the viscosity of the solvent or emulsion and provide gel strength to the solvent or emulsion. The second class of polymers or additives can be generally termed "flow control" polymers or additives, which assist in controlling the flow characteristics of the compositions used in the dressings of this invention.

Gel strength can be measured by the relationship between the viscosity of the composition and temperature. Network polymers show a "plateau" in this type of measurement, i.e., the viscosity of the composition displays little or no change over a wide temperature range. The value of the viscosity at this plateau is defined as the gel strength. Preferably, in the compositions used in the dressings of this invention, the gel strength should be from about 1,000 to about 10,000 poise over a temperature range of from about 50° C. to about 95° C.

Gel strength is particularly important in manufacturing and processing sterile bandages and wound dressings, especially if high temperatures are to be encountered in the manufacturing process. If the dressings or bandages are to be subjected to high temperature sterilization (about 175° to about 180° F., 80°–82° C.), as would be the case with ethylene oxide sterilization for example, the dressings of the invention should be able to withstand such temperatures without causing the structured ointment compositions to readily flow into the primary packaging or into the uncoated regions of the absorbent substrate. Such ready flow might compromise sterility or otherwise adversely affect the absorptive characteristics of the dressing. Alternatively, it will be recognized that the difficulties of high temperature sterilization may be avoided by resorting to low temperature sterilization techniques such as irradiation sterilization.

Preferably, the polymers that are useful in the compositions used in the dressings of this invention to create gel strength are block copolymers. Di-, tri- and multiarm block copolymers of polystyrene and synthetic rubber are especially useful as network polymers in the dressings of this invention. The rubber block of the aforesaid block copolymer is preferably a polymer of isoprene, ethylene-butadiene, ethylene-propylene and the like or combinations thereof. Examples of such polymers are KRATON di- and tri-block copolymers, commercially available from the Shell Chemical Company, and the like. The KRATON polymers are described by Shell as elastomers which have a combination of high strength and low viscosity. These polymers contain block segments of styrene monomer units and rubber monomer units. KRATON G-1702, a di-block copolymer of styrene and (ethylene-propylene), is especially useful in this regard.

Polyacrylic acids which are slightly crosslinked such as the CARBOPOLs, commercially available from B.F. Goodrich, are also useful as network polymers in the products of this invention. Polyacrylic acids of this type and other polymers such as polyethylene oxide, cellulosics and polysaccharides act as network polymers and may also contribute to maintaining moisture in the wound. The Aquasorb-D series of polymers are modified guar gums available from Hercules Corporation, and are examples of modified polysaccharides which are useful in the compositions used in the dressings of this invention for maintaining gel strength. Preferably, one CARBOPOL polyacrylic acid that would be useful in the compositions used in the dressings of this invention is CARBOPOL 934P, a polymer of acrylic acid crosslinked with allyl sucrose.

The second class of polymers or additives useful in the compositions used in the dressings of this invention are the "flow control polymers", which are chosen to assist in controlling flowability of the composition at or about room temperature. These materials also aid in film-forming capacity, affording a more film-like structure to the dressings of this invention as opposed to a gel-like structure. Film-like characteristics are important so as to lend greater integrity to the dressing under manufacturing conditions. However, the flowability should not be so great as to permit the compositions to migrate from their desired positions on a dressing while the dressing is in use on a wound.

The flow control agents, polymers or additives useful in the compositions of this invention also assist in achieving an "ointment feel" to the dressings of the invention. This "ointment feel" can be quantified as the value of the shear elastic compliances and loss compliances of the compositions measured at skin temperatures, (approximately 35° C.) at a testing frequency of 10 radians/second as measured on a Rheometrics RDS 7700 rheometer.

Petrolatum, for example, has a very high shear compliance, greater than $5\times10^{-5}$ $cm^2$/dyne and has a loss compliance greater than $1\times10^{-5}$ $cm^2$/dyne. Though petrolatum has an "ointment feel", it is also extremely fluid and therefore unacceptable for use by itself in the dressings of this invention. The balance of "controlled flow" and "ointment feel" falls within the following desirable band of shear compliances: the elastic compliance ranges from about $2\times10^{-6}$ to about $20\times10^{-6}$ $cm^2$/dyne and the loss compliance ranges from about $3\times10^{-6}$ to about $20\times10^{-6}$ $cm^2$/dyne. Above this range, the compositions may have an ointment feel, but their flowability is very high. Below this range, the flow is well controlled, but the composition has a considerably reduced ointment feel. The desired balance of controlled flow and ointment feel is achieved within this range.

Preferably, the flow control polymers assist in assuring that, at low temperatures, the viscosity dependence of the compositions is linear on a semi-log plot. This indicates that the compositions used in the dressings of this invention have a predictable, controlled viscosity at ambient, usage temperatures.

The flow control polymers that assist in controlling flow at ambient temperatures are preferably selected from polymers such as polyolefins. The flow control polymers are preferably homopolymers, copolymers or polymers composed of several monomers, and they are preferably not crosslinked. More preferably, this second class of polymers or additives includes the following: polyvinyl acetate; ethylene-vinyl acetate copolymer; polyalkylenes such as polyisobutylene, ethylene-propylene copolymers and polyethylenes and the like. The tri-block copolymers of polystyrene and synthetic rubber mentioned above for use as network polymers also appear to function as flow control polymers. KRATON G-1650, a tri-block copolymer of styrene, ethylene-butylene and styrene, is especially useful in this regard.

The flow control polymers or additives may also affect the "tack" of the composition, either tackifying or detackifying the composition, depending upon the polymers chosen and their concentrations. For example, polyethylenes added at a concentration of at least about 5% may aid in detackifying a composition whereas ethylene-vinyl acetate copolymer added at a concentration of at least about 5% may increase the tackiness of the composition.

Additional additives may also be introduced into the compositions used in the dressings of the invention to influence the "feel" of the final product. The composition preferably mimics the sensation of ointment products as fully as possible, in order to ensure that the consumer who is accustomed to prior ointment products is comfortable wearing the dressing comprising the composition. For example, silicone waxes, common emollients known to those of skill in the art (e.g., polyethylene glycol esters, most preferably, having fatty acid such as stearate or palmitate functional end-groups), fatty acid esters such as a stearate or palmitate esters, fatty alcohols such as stearyl alcohol or the like may be used for this purpose in the dressings of the invention. Dow Corning 580 wax, available from Dow Corning Corp. of Midland Mich., is a mixture of stearoxytrimethylsilane and stearyl alcohol. This wax is especially useful to enhance the ointment feel of the composition by reducing the drag created by the network and flow control polymers.

The dressings of the invention are ideally suited to deliver one or more active ingredients such as therapeutics to the surface of the skin. Illustrative classes of active ingredients that may be delivered to the skin via the dressings of the invention include antibiotics, analgesics, antipyretics, antimicrobials, antiseptics, antiallergics, anti-acne, anesthetics, anti-inflammatories, hemostats, cosmetics, vitamins, vasodilators, emollients, pH regulators, antipruritics, counterirritants, antihistamines and steroids. Specific active ingredients that may be delivered to the skin via the dressings of the invention include chlorhexidine, neomycin sulfate, polymyxin-B sulfate, zinc bacitracin, benzalkonium chloride, cetylpyridinium chloride, bupivacaine, tetracaine, cincaine, lidocaine, benzocaine, silver sulfadiazine, hydrocortisone, metandienone, trypsin, tolazoline, heparin, pramoxine, aloe vera, tretinoin, retinol, retinaldehyde, menthol, capsaicin, alpha hydroxy acids and vitamins such as Vitamin E.

When contained in the dressings of the invention, one or more active ingredients may be contained primarily or exclusively in the absorbent substrate of the dressing or primarily or exclusively in the composition used in the discontinuous coating. Alternatively, active ingredients may be distributed both in the absorbent substrate and in the discontinuous coating of the dressing.

When multiple active ingredients are contained in the dressings of the invention, all actives may be present in both the coating composition and in the substrate. Alternatively, certain actives may be predominantly or exclusively present in one phase (e.g., the substrate) while other actives may be present predominantly or exclusively in the other phase (e.g., the coating).

The dressings of the invention contain two distinct regions or phases from which actives may be dispensed via two different mechanisms. Active ingredients contained in the coating composition are dispensed from the dressing via an active mechanism, in which active ingredients are readily available to the skin even in the absence of moisture. Active ingredients are dispensed from the absorbent substrate portion of the dressing via a passive mechanism, whereby actives are delivered from the substrate primarily in the presence of moisture such as wound exudate. Accordingly, it is possible to design dressings which are specifically formulated to take advantage of these different mechanisms. For example, one embodiment of the dressing of the invention contains both skin soothing e.g., aloe vera, and hemostatic active ingredients. Since hemostatic agents are only necessary in the presence of an active, i.e., bleeding wound, hemostatic agents are desirably incorporated in the substrate portion of the dressing from which they may be activated by blood or wound exudate. In contrast, the soothing agent may be incorporated in the coating portion of the dressing so as to be available to the wound site during the subsequent wound healing phase after exudation from the wound has ceased.

The ability to localize an active ingredient in different portions of a dressing also permits the construction of a dressing containing actives that might be mutually incompatible. For example, active A may be contained in the substrate portion of the dressing while active B, which is incompatible with active A, might be contained in the coating portion of the dressing. An example of such a dressing is one which incorporates the active ingredients zinc bacitracin and benzalkonium chloride. While these ingredients are mutually incompatible when they are present together in a single phase, a dressing which incorporates the ingredients in different phases, e.g., zinc bacitracin in the coating composition and benzalkonium chloride in the substrate material, is expected to be stable. The technique of partitioning two or more actives between different portions of a dressing provides a means for fabricating dressings in which two or more incompatible actives are made accessible to a wound from the same dressing, in a manner that was not heretofore available in prior art dressings.

The compositions used in the dressings of the invention may be advantageously colored with dyes or other coloring agents. Since the dressings of the invention may, in principle be made with a variety of different active ingredients intended to accomplish a variety of different functions, the ability to color-code the compositions provides an easy method to differentiate different compositions, both during manufacturing and in use by consumers.

As indicated hereinabove, the compositions used in the coatings in the dressings of the invention are substantially non-adherent to the skin. Accordingly, in use, the dressings may be held adjacent to the skin by wrapping a web such as a gauze around the body portion containing the dressing. Alternatively and preferably, the dressing of the invention is part of an adhesive bandage in which the dressing is secured to an adhesive-coated backing material.

Backing materials useful in the bandages of the invention include monolithic films, apertured films, foams, woven fabrics, nonwoven fabrics and composites thereof. In the case of films, the backing may be composed of any of the polymers known to be useful as backing materials. Such polymers include plasticized PVC, polyolefins such as polyethylene or polypropylene, and polyurethane. Perforated or apertured films are the preferred backing materials for the bandages of the invention.

The invention will now be illustrated by way of the following examples. The examples are merely illustrative and are not intended to limit the scope of the invention.

EXAMPLE 1

Preparation of Coating Composition

The semi-solid coating composition was made by transferring 3196 lbs. of Super White Petrolatum (Penreco division of Pennzoil Products Company, Karns City, Pa.) into a 1000 gallon stirred and heated tank. 0.4 lbs. of butylated hydroxy toluene (PMC, Inc., Rocky River, Ohio) were added. The tank was heated to 275° F. with mixing and 280 lbs. of Kraton G1702 (Shell Chemical Company, Houston, Tex.) and 80 lbs. of Kraton G1650 (Shell) were added. The ingredients were then mixed for three hours at 275° F. at which point the mixture was fully homogenous. The mixture was allowed to cool overnight to room temperature. The next morning, the mixture was re-heated to a temperature of about 230° F. with mixing. 400 lbs. of Dow Corning 580 Wax (Dow Corning Corp., Midland Mich.), pre-heated to 180° F., was added. 4 lbs. of Vitamin E acetate (Hoffmann-La Roche, Paramus, N.J.) followed by 40 lbs. of Mineral Oil Extract #101, an aloe vera mineral oil extract (Florida Food Products, Inc., Eustis, Fla.), were added. The mixture was mixed at about 230° F. for one and a half hours until it was homogeneous. The mixture was discharged into storage drums where it was allowed to cool to ambient temperature. The mixture had the following composition:

| Component | Concentration (weight %) |
|---|---|
| Petrolatum | 79.9 |
| Kraton G1702 | 7.0 |
| Kraton G1650 | 2.0 |
| Dow Corning 580 wax* | 10.0 |
| Vitamin E acetate | 0.1 |
| Aloe Vera Extract | 1.0 |
| BHT | 0.01 |
| Total | 100 |

*A mixture of stearoxytrimethylsilane and stearyl alcohol

EXAMPLE 2

Figure 5:
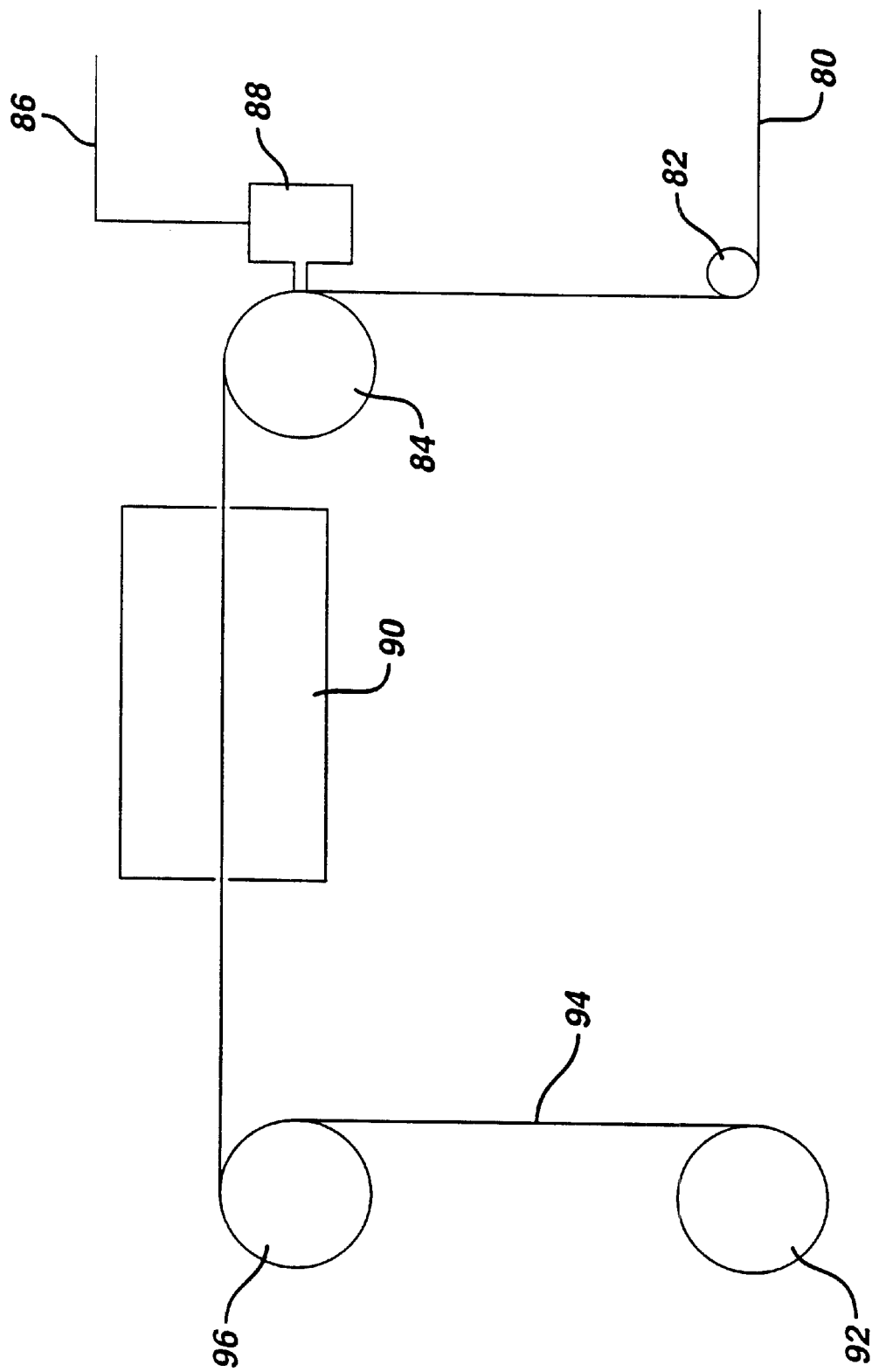
FIG. 5 depicts an apparatus for making the dressing of the invention.

Preparation of a Continuous Roll of Dressing of the Invention by Discontinuous Coating of the Ointment Composition on an Absorbent Substrate The equipment used to apply a discontinuous coating of the ointment composition to a web of the absorbent substrate in the preparation of the dressings and bandages of the invention is shown in FIG. 5. A 5 gallon pail of the ointment composition of Example 1 was placed in a Model 505 Bulk Melter Applicator (Nordson Corp., Boothwyn, Pa.) (not shown). The melter comprised a platen heater which heats the upper surface of the ointment composition contained in the pail. The platen was heated to a temperature of about 133° F. to melt the composition contained in the uppermost portion of the pail. The ointment composition was pumped via a gear pump (not shown) located in the Melter-Applicator via line 86 to slot die 88. The die 88 was maintained at a temperature of about 128° F. during the coating operation. A ⅞"-wide web of absorbent substrate 80 was let off a supply roll using a conventional unwinding system (not shown). The web was a needle-punched nonwoven comprising 65% rayon fibers and 35% polyamide fibers coated with a coating of low density polyethylene on one side thereof. The web had a basis web of 140 g/m$^2$ and a thickness of 0.85 mm, and was available as nonwoven M1541 from the Freudenberg Company of Weinheim, Germany. Prior to coating with the ointment composition of Example 1, the web of substrate material was pre-impregnated with benzalkonium chloride at an add-on of 0.045 mg/cm$^2$ by dipping the web into a 0.46% solution of benzalkonium chloride in water, passing the web between nip rolls to remove excess benzalkonium chloride solution and drying the web in a heating oven. The web was removed from a supply roll contained on a conventional web unwind/tensioning apparatus of the type well known in the art (not shown). It was subsequently directed around roller 82 onto roller 84. The ointment composition was extruded from die 88 in the form of four stripes, each of which were ⁵⁄₃₂" in width, the distance between stripes being ¹⁄₁₆", onto the uncoated side of the absorbent nonwoven substrate 80. The ointment was applied onto the substrate web 80 at a coating weight of 3.96 g per linear meter. Following coating with the ointment composition, the web passed through a controlled temperature chamber 90 containing air cooled to 10° to 30° F. to cool the web to room temperature. The web was then directed to take-up roll 96 where it was wound on a spool along with a layer of interliner material 94 composed of silicone-coated release paper let off of supply roll 92.

EXAMPLE 3

One Embodiment of a Bandage of the Invention

Figure 6:
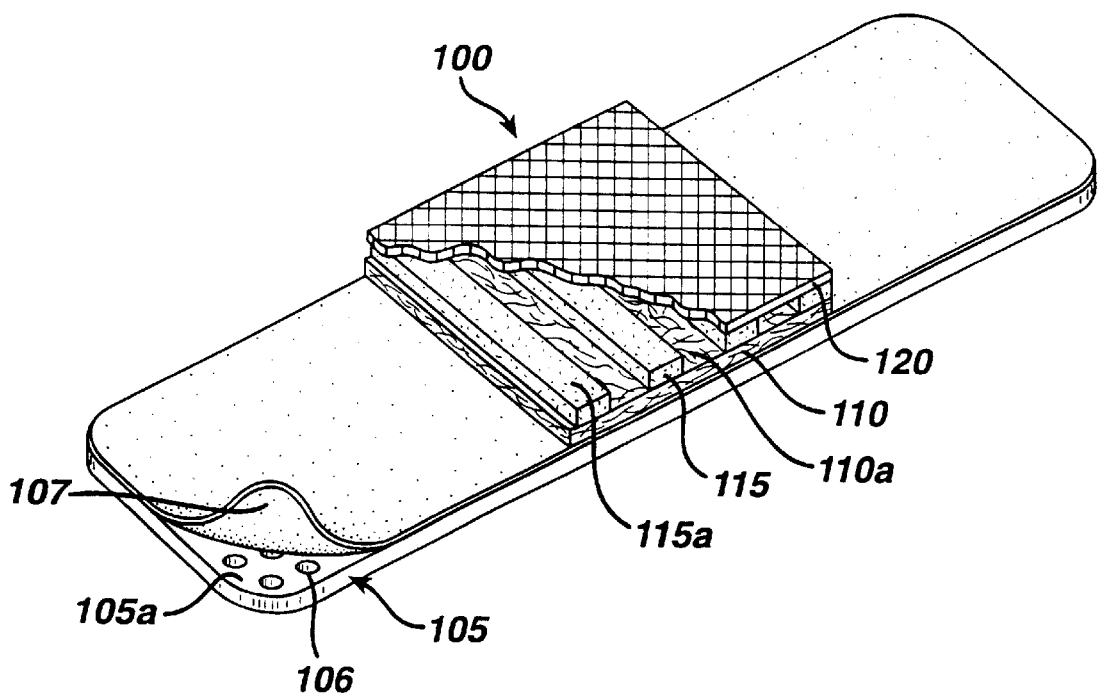
FIG. 6 shows a perspective view with parts cut away of an adhesive bandage of the invention.

An adhesive bandage is made using the dressing described in Example 2. This adhesive bandage is illustrated in FIG. 6 of the drawings. Adhesive bandage 100 comprises a backing material 105 having apertures 106 therein; an absorbent substrate 110; a discontinuous coating of an ointment-like composition 115; and a porous covering material 120. The upper surface 105a of the backing material is coated with a layer of a pressure-sensitive acrylic adhesive 107. It will be understood that any of the adhesives well known in the art for use with adhesive bandages may be used in place of this adhesive. The adhesive may, if desired, be deposited on the backing layer in a continuous or discontinuous pattern rather than as an overall coating as illustrated in the drawing.

As is further illustrated in the drawings, substrate material 110 is preferably provided in the form of a fibrous pad which is centered from end-to-end of the backing material and extends from one side of the backing material to the other. Substrate material 110 is secured to the backing material by the aforementioned adhesive 107. It will be understood that the substrate material may comprise nonwoven fabrics other the one described above. In addition, other materials, such as foams, woven fabrics (e.g., gauze), knitted fabrics and the like may be used. Alternatively, substrate material may be covered or wrapped with a thin layer of nonwoven material or with a porous mesh, film or scrim.

As will also be seen in the drawings, the upper surface 110a of fibrous substrate material 110 carries and has adhered thereto ointment-like composition 115. The composition is coextensive in width with substrate material 110 but is discontinuous in its length. In addition to absorbing wound exudate, the substrate material functions to support the ointment-like composition which overlies its upper surface. In addition, the absorbent substrate material tends to provide a desirable cushioning effect when the adhesive bandage is applied over a wound site. Since the ointment-like composition is discontinuously coated on the surface of the absorbent substrate, the substrate is available to absorb moisture-containing fluids such as wound exudate during use.

The upper surface 115a of ointment-like composition 115 is covered by a porous covering material 120. In the specific embodiment of this Example, porous covering material 120 comprises a porous polyethylene film available from Hercules, Inc., Wilmington, Del., U.S.A. under the designation DELNET X-550. Other porous covering materials can be used in place of the aforementioned porous polyethylene films available under the DELNET name. For example, the porous covering material can be made of polyvinyl chloride, polypropylene, polyester, nylon or the like polymeric materials instead of polyethylene.

The ointment-like composition 115 used in adhesive bandage 100 of this Example is the composition set forth in the foregoing Example 1. The occlusive composition 115 is applied to substrate material 110 in accordance with the procedure set forth in Example 2 hereinabove. The porous covering material 120 overlies upper surface 115a of occlusive composition 115 and is coextensive in length and width with the underlying substrate material 110.

Figure 7:
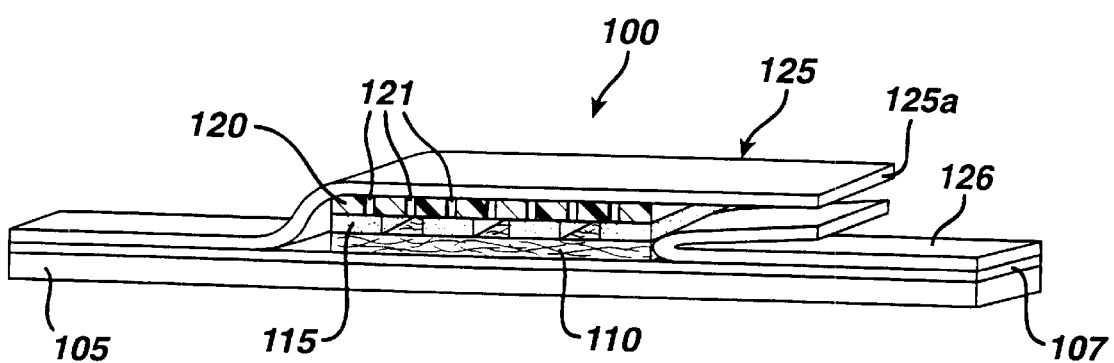
FIG. 7 is a side view, of the bandage of FIG. 6 wherein the bandage further comprises release tabs.

Release tabs 125, 126 which comprise silicone-coated polystyrene, are placed over the exposed portions of adhesive 107 and the upper surface of porous covering material 120 in the fashion shown in FIG. 7 of the drawings.

Figure 8:
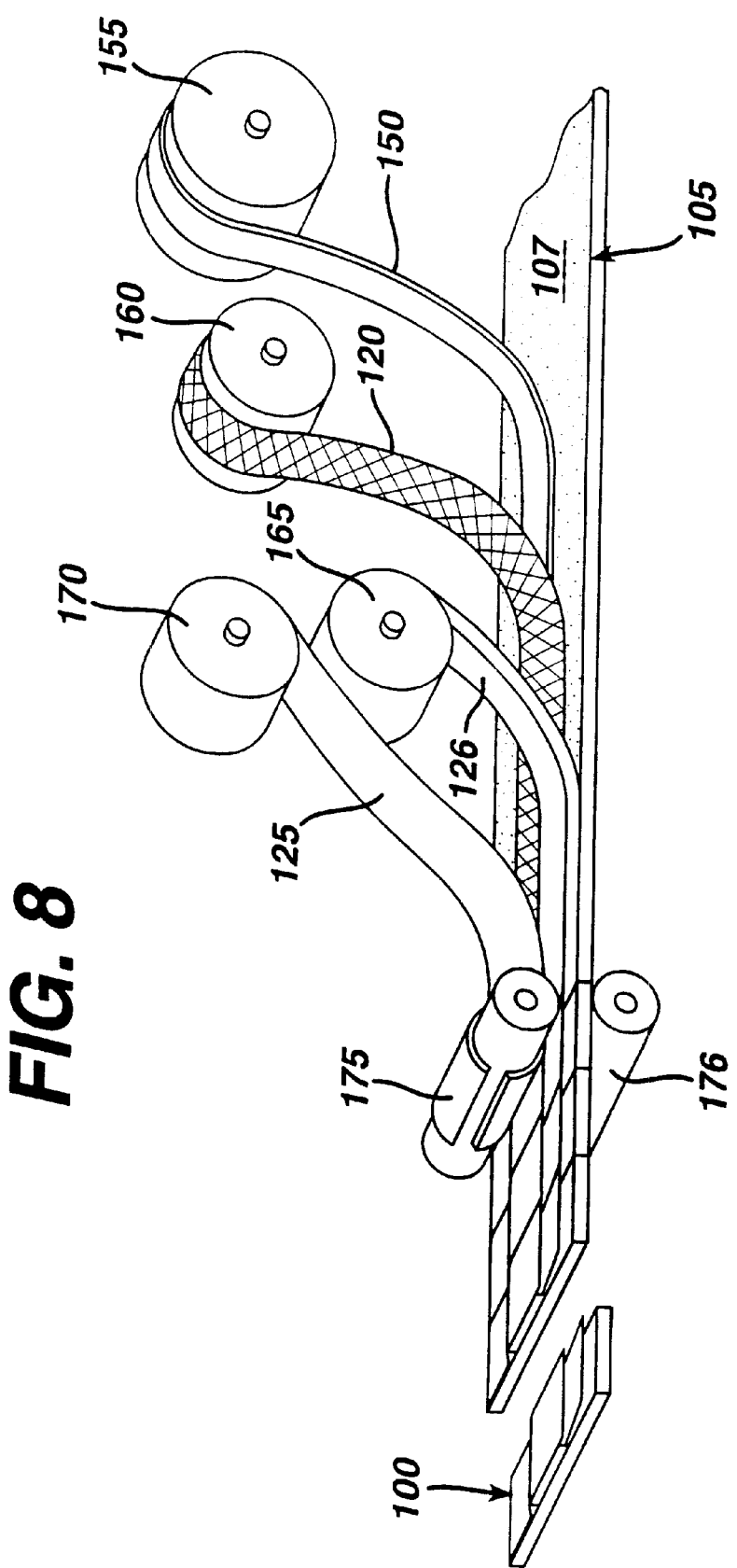
FIG. 8 is a schematic depicting the manufacture of the bandage of FIG. 7.

The adhesive bandage shown in FIG. 7 is made according to a process in which the bandage is oriented at right angles to the direction of travel of the raw materials through the manufacturing apparatus. Briefly, as shown in FIG. 8, the backing material 105 coated with adhesive 107 is conveyed, from right-to-left as viewed in FIG. 8, on top of a conveyor belt (not shown). A web 150 comprising the substrate material 110 onto which the ointment-like composition 115 had been previously applied by the extrusion coating process of Example 2 is led off roll 155 and placed on top of the adhesive coated backing material 105.

Porous covering material 120 is led off supply roll 160 and placed on top of web 150. It will be understood that, in the process being described, the width of covering material 120 corresponds substantially to the width of web 150. Release material 126, supplied from roll 165, is folded to the configuration shown in FIG. 7 and applied to the exposed adhesive area at one side of the adhesive coated backing material. Release material 125, supplied from roll 170, is then applied so as to cover the exposed adhesive area at the other side of the adhesive coated backing material as well as the upper surface of porous covering material 120. Release material 125 extends beyond the edge of the porous covering material to provide a grasping tab 125a as illustrated in FIG. 7 of the drawings.

The combined raw materials, assembled as just described, are then passed through the nip of cutter rollers 175, 176. Rollers 175, 176 perform two functions, i.e., they compress the previously assembled raw materials at a pressure of about 10–20 pounds per square inch and, at the same time, cut the traveling, assembled raw materials into individual adhesive bandages 100. The individual adhesive bandages are subsequently wrapped, packaged and sterilized, all according to procedures which are well known in the art.

The manner of making bandages as described hereinabove gives rise to bandages wherein the width of the dressing is coextensive with the width of the bandage. In alternate embodiments, bandages of the invention comprise dressings wherein the bandages are neither coextensive in length or width with their contained dressings. Rather, in these embodiments, the dressing is both narrower in width and shorter in length than the adhesive-coated backing material to which it is attached. In such configurations, these bandages are termed "island bandages" or "island dressings", and are also considered to be within the scope of the bandages and dressings of the invention.

EXAMPLE 4

Another Embodiment of the Bandage of the Invention

Figure 9:
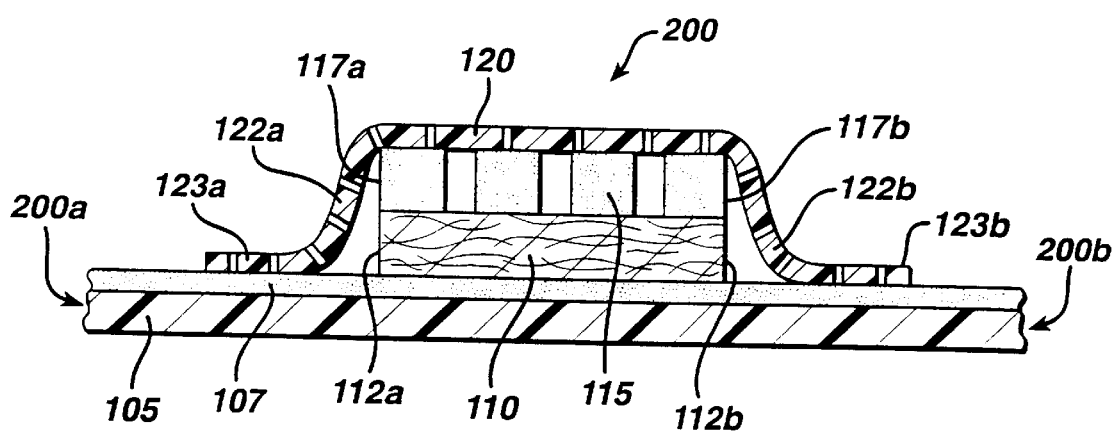
FIG. 9 is a longitudinal section of another embodiment of the bandage of FIG. 7 wherein the porous covering material has downwardly extending portions and laterally extending tab portions.

Referring now to FIG. 9, there is illustrated in longitudinal section another embodiment of an adhesive bandage 200 of the invention in which porous covering material 120 has been given an alternative configuration. As was the case with adhesive bandage 100 illustrated in FIG. 6, adhesive bandage 200 comprises backing 105; adhesive layer 107; absorbent substrate material 110; ointment-like composition 115; and porous covering material 120. In bandage 100 disclosed in FIG. 6, porous covering material 120 was coextensive in its length and width with fibrous substrate material 110. In the alternative embodiment illustrated in FIG. 9, porous covering material 120 comprises downwardly extending portions 122a, 122b and longitudinally extending tab portions 123a, 123b. Downwardly extending portions 122a, 122b serve to cover the ends 112a, 112b, respectively, of fibrous substrate material 110 and the ends 117a, 117b, respectively, of ointment-like composition 115. As will be seen by reference to FIG. 9, ends 112a and 117a face end edge 200a of adhesive bandage 200, while ends 112b and 117b face end edge 200b of the adhesive bandage. Tab portion 123a of porous cover material 120 extends longitudinally for a short distance, e.g., about one-eighth of an inch, toward end edge 200a of bandage 200 while tab portion 123b extends a short distance toward end edge 200b.

The advantage of providing porous cover material 120 with downwardly extending portions 122a, 122b and tab portions 123a, 123b is that longitudinal movement of ointment-like composition 115 (i.e., movement toward either or both of ends 200a, 200b of bandage 200) is substantially prevented.

In addition, this configuration of porous covering material 120 helps to insure that substrate material 110 remains firmly in its centered location between ends 200a, 200b of the bandage.

EXAMPLE 5

Microbiocidal Activity of the Bandage of the Invention Comprising Benzalkonium Chloride The purpose of this test was to determine whether the efficacy of the benzalkonium chloride contained within the absorbent substrate of a bandage of the invention would be adversely affected when a portion of the skin-facing surface of the absorbent substrate contained a discontinuous coating of an ointment-like composition. The specimens tested were the bandages of Example 4 comprising the dressing of Example 2. Test samples 2.5 cm×2 cm were cut from the bandages so as to remove the longitudinally extending adhesive strip portions that extended beyond the boundary of the dressing portion of the bandage.

The microbiocidal activity of the benzalkonium chloride in the dressing was tested by placing samples of the dressing on a peptone-casein-soya agar growth medium contained in petri dishes having an area of 64 square centimeters that had been inoculated with certain microorganisms. The test samples were placed in the dishes so that the skin facing side of the dressing contacted the agar medium. The following microorganisms were used:

| Organism | CNCM Reference Number |
| --- | --- |
| Escherichia coli | 54127 |
| Staphylococcus aureus | 53154 |
| Streptococcus foecalis | 5855 |
| Pseudomonas aeruginosa | A 22 |
| Mycobacterium smegmatis | 5855 |

The bactericidal suspensions for seeding of the prepared petri dishes were taken from cultures in their exponential growth phase. The concentration of each suspension was determined according to an AENOR (Association Francaise Normalisation) standard method using spectrophotometry at 620 nm. Suspensions of the desired concentration were then prepared by successive dilution to give seeding stock solutions.

A standard volume of the seeding stock solution was placed in the center of each prepared petri dish and spread with the help of a spreader. The inoculated plates were dried off in a drying oven at 37° C. for 30 minutes. The dressings were placed on top of the medium in the manner described above, and the petri dishes were then incubated for a total of 24 to 48 hours at 37° C. Dishes were removed from the incubator periodically and the extent of bacterial growth underneath the dressing was measured. The results are indicated in the table below:

| Organism | Initial Organism Concentration (CFUs/cm$^2$*) | Contact time | | | Full incubation |
| --- | --- | --- | --- | --- | --- |
| | | 10 min | 1.5 hr | 5 hr | |
| Escherichia coli | 8.2 × 10$^1$ | TMTC | TMTC | 0 | 0 |
| | 8.2 × 10$^3$ | TMTC | TMTC | 0 | 0 |
| Streptococcus foecalis | 2.7 × 10$^6$ | 0 | 0 | 0 | 0 & Diff |
| Staphylococcus aureus | 8.6 × 10$^5$ | 0 & Diff | 0 & Diff | | 0 & Diff |
| Mycobacterium smegmatis | 9.5 × 10$^3$ | 0 & Diff | 0 & Diff | | 0 & Diff |

-continued

| | Initial Organism Concentration | Contact time | | | Full |
|---|---|---|---|---|---|
| Organism | (CFUs/cm²*) | 10 min | 1.5 hr | 5 hr | incubation |
| Pseudomonas aeruginosa | 6.8 × 10⁵ | | TMTC | | TMTC |

*cfu = colony forming units
TMTC = too many to count, indicating marginal effect of the antiseptic on the microorganism
0 = No growth of colonies under the dressing. Bactericide in dressing is effective against the microorganism.
Diff = diffusion of the antiseptic beyond the boundary of the dressing to kill colonies adjacent to the dressing.

The test results indicate that the benzalkonium chloride antiseptic in the dressing and bandage of the invention exhibits significant bactericidal activity against all of the microorganisms tested with the exception of Pseudomonas aeruginosa. This is not surprising, since quaternary antiseptics like benzalkonium chloride are known to be less effective against Pseudomonas relative to other micro-organisms. The results indicate that coating of the ointment-like composition on the absorbent substrate does not decrease the activity of the active ingredient contained within the substrate.

The antiseptic in the substrate remains fully effective, indicating that in contrast to prior art dressings wherein the coating composition is continuously coated over a support, the discontinuous coating on the dressing of the invention permits access to the underlying substrate and to active ingredients contained therein.

What is claimed is:

1. A bandage comprising:
   a. an absorbent substrate having a first skin-facing surface and a second opposing surface;
   b. a discontinuous coating of a semi-solid composition having an ointment feel overlying a portion of the first surface of said absorbent substrate;
   c. a first active ingredient contained within said absorbent substrate;
   d. a second active ingredient contained within said discontinuous coating;
   e. a backing material; and
   f. a layer of adhesive on one surface of said backing material, said adhesive layer securing said absorbent substrate to said backing material; wherein
   said absorbent substrate is useful as a passive dispenser of at least one active ingredient, said coating is substantially non-adherent to the skin, said coating is useful as an active dispenser of at least one active ingredient and said active ingredients are intended to deliver one or more therapeutic benefits to the skin.

2. The bandage of claim 1 wherein said active ingredients are selected from antibiotics, analgesics, antipyretics, antimicrobials, antiseptics, antiallergics, anti-acne, anesthetics, anti-inflammatories, hemostats, cosmetics, vitamins, vasodilators, emollients, pH regulators, antipruritics, counterirritants, antihistamines and steroids.

3. The bandage of claim 1 wherein said active ingredients are selected from chlorhexidine, neomycin sulfate, polymyxin-B sulfate, zinc bacitracin, benzalkonium chloride, cetylpyridinium chloride, bupivacaine, tetracaine, cincaine, lidocaine, benzocaine, silver sulfadiazine, hydrocortisone, metandienone, trypsin, tolazoline, heparin, pramoxine, aloe vera, tretinoin, retinol, retinaldehyde, menthol, capsaicin, alpha hydroxy acids and Vitamin E and its derivatives.

4. The bandage of claim 1 wherein said first active ingredient is an antiseptic and said second active ingredient is selected from antipruritics, antibiotics, anesthetics, anti-inflammatories or mixtures thereof.

5. The bandage of claim 4 wherein said second active ingredient is an antipruritic.

6. The bandage of claim 1 wherein said first active ingredient comprises benzalkonium chloride and said second active ingredient comprises aloe vera.

7. The bandage of claim 6 wherein said discontinuous coating further comprises Vitamin E or one or more of its derivatives.

* * * * *